United States Patent [19]

Nash, III et al.

[11] 4,385,122

[45] May 24, 1983

[54] ANTHRACYCLINE ANTIBIOTICS PRODUCED BY STREPTOSPORANGIUM FRAGILE

[75] Inventors: Claude H. Nash, III, Audubon; Marcia C. Shearer, Conshohocken; Kenneth M. Snader, Hatboro; Joseph R. Valenta, Strafford; David Cooper, Phoenixville, all of Pa.

[73] Assignee: SmithKline Beckman Corporation, Philadelphia, Pa.

[21] Appl. No.: 295,042

[22] Filed: Aug. 21, 1981

Related U.S. Application Data

[62] Division of Ser. No. 171,852, Jul. 24, 1980, Pat. No. 4,293,546.

[51] Int. Cl.³ .................... C12N 1/20; C12P 27/00; C12P 1/06; C12R 1/62
[52] U.S. Cl. .................................. 435/253; 435/64; 435/169; 435/907
[58] Field of Search ................ 435/169, 907, 253, 64, 435/78; 424/119, 115

[56] References Cited

U.S. PATENT DOCUMENTS 3,723,411 3/1973 Brockmann et al. ............... 424/108
4,293,546 10/1981 Nash et al. ......................... 424/119

OTHER PUBLICATIONS

The Merck Index, 9th ed., 1976, Merck and Co. Inc., Rahway, N.J., pp. 1062–1063.

Primary Examiner—Thomas G. Wiseman
Assistant Examiner—Kathleen S. McCowin
Attorney, Agent, or Firm—Joseph F. DiPrima; Richard D. Foggio; Alan D. Lourie

[57] ABSTRACT

A novel anthracycline antibiotic complex, fragilomycin complex, is produced by the cultivation of a fermentation broth containing Streptosporangium fragile Shearer sp. nov. ATCC 31519 microorganisms in an aqueous nutrient medium under submerged aerobic conditions. The fragilomycin complex and its major bioactive component, fragilomycin A, exhibit antibiotic activity.

2 Claims, 3 Drawing Figures

ANTHRACYCLINE ANTIBIOTICS PRODUCED BY STREPTOSPORANGIUM FRAGILE

This is a division of application Ser. No. 171,852 filed July 24, 1980 now U.S. Pat. No. 4,293,546.

SUMMARY OF THE INVENTION

This invention relates to new anthracycline antibiotics and the production and recovery thereof. This invention also relates to the new microorganism, *Streptosporangium fragile* Shearer sp. nov. SK&F-BC2496 (ATCC 31519). More particularly, this invention relates to an anthracycline antibiotic, designated herein fragilomycin complex, said complex being produced by cultivating S. fragile in an aqueous nutrient medium containing assimilable sources of nitrogen and carbon, under submerged aerobic conditions until a substantial amount of fragilomycin complex is produced by said microorganism in said culture medium and optionally, recovering fragilomycin complex from the culture medium. Also provided by the present invention is a novel bioactive anthracycline component of the fragilomycin complex, fragilomycin A, which is prepared by the separation and isolation of the individual antibiotic compounds of the fragilomycin complex by chromatographic means. The anthracycline antibiotic, fragilomycin complex, and its major bioactive component, fragilomycin A, all exhibit antibacterial activity.

DETAILED DESCRIPTION

The new anthracycline antibiotics, fragilomycin complex and its major bioactive component, fragilomycin A, are produced by the fermentation of a new member of the genus Streptosporangium, designated *Streptosporangium fragile* sp. nov. SK&F BC-2496. The above-noted microorganism was obtained from a soil sample collected from a cultivated field lying fallow after a paddy crop in the Northern Province of Sri Lanka in the village of Anaikota, about five miles from Jaffna. A culture of the microorganism has been deposited in the American Type Culture Collection, Rockville, Md. as a type culture under accession number ATCC 31519.

As in the case of many antibiotic-producing cultures, the fermentation of *S. fragile* results in the production of a mixture of component substances. Thin layer chromatography of the fragilomycin complex on silica gel (Whatman K-5) developed with 15 percent methanol in methylene chloride affords three distinct bioactive components at $R_f$ values of 0.26, 0.34 and 0.51. The bioactive component with the $R_f$ value of 0.51 is fragilomycin A, hereinafter more fully described.

The major bioactive anthracycline component, fragilomycin A, has been isolated from the anthracycline antibiotic, fragilomycin complex, produced by the above-mentioned microorganism.

Fragilomycin A has been determined to have the following partial structural formula:

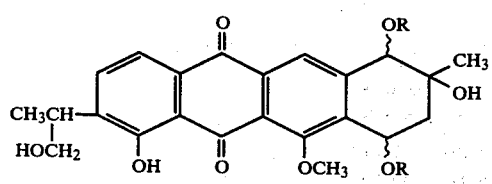

wherein R represents sugars of unassigned structure. The above structure fragilomycin A was elucidated by analysis of the following physiochemical properties and by degradative studies.

Figure 1:
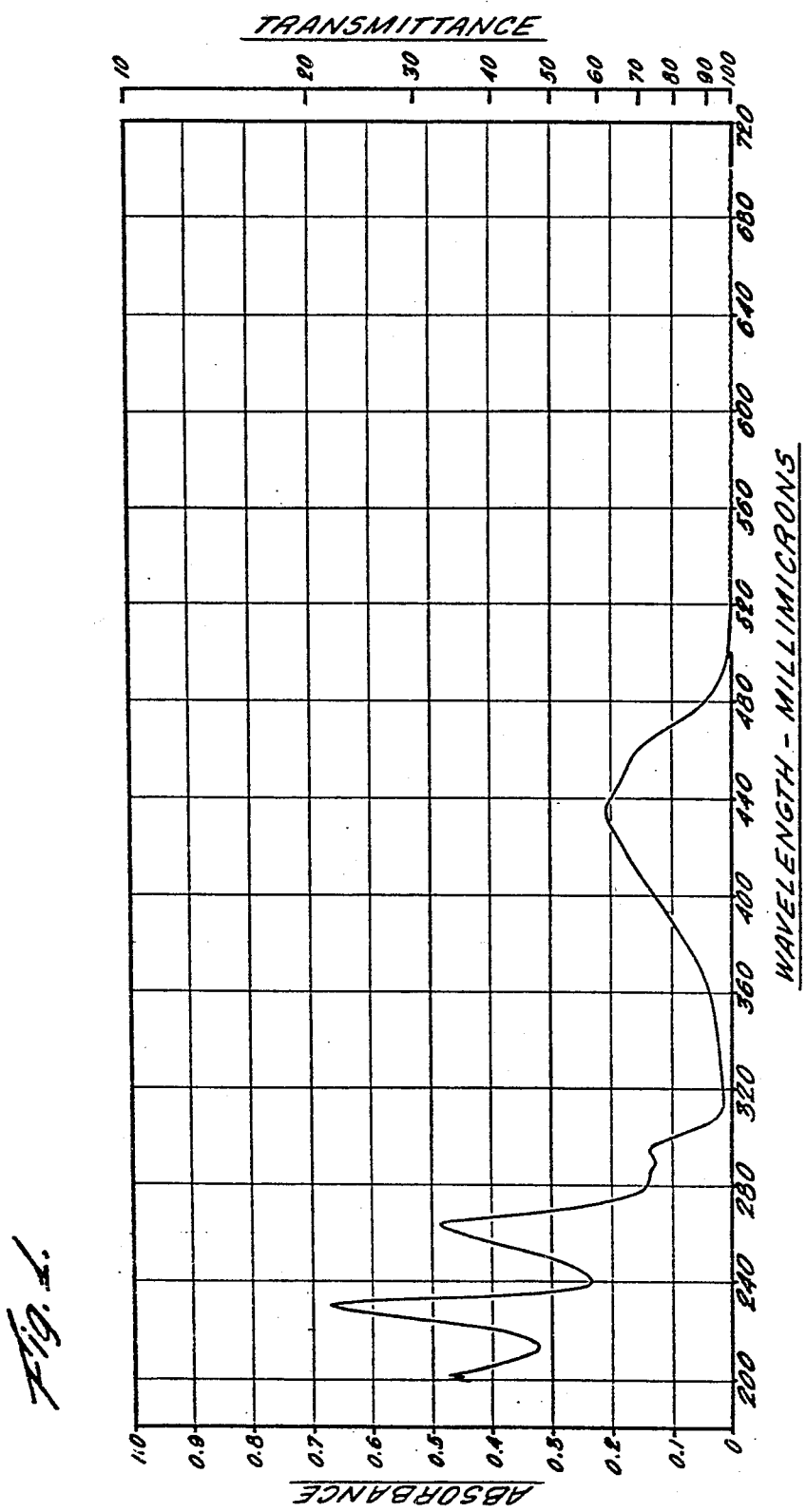
Figure 2:
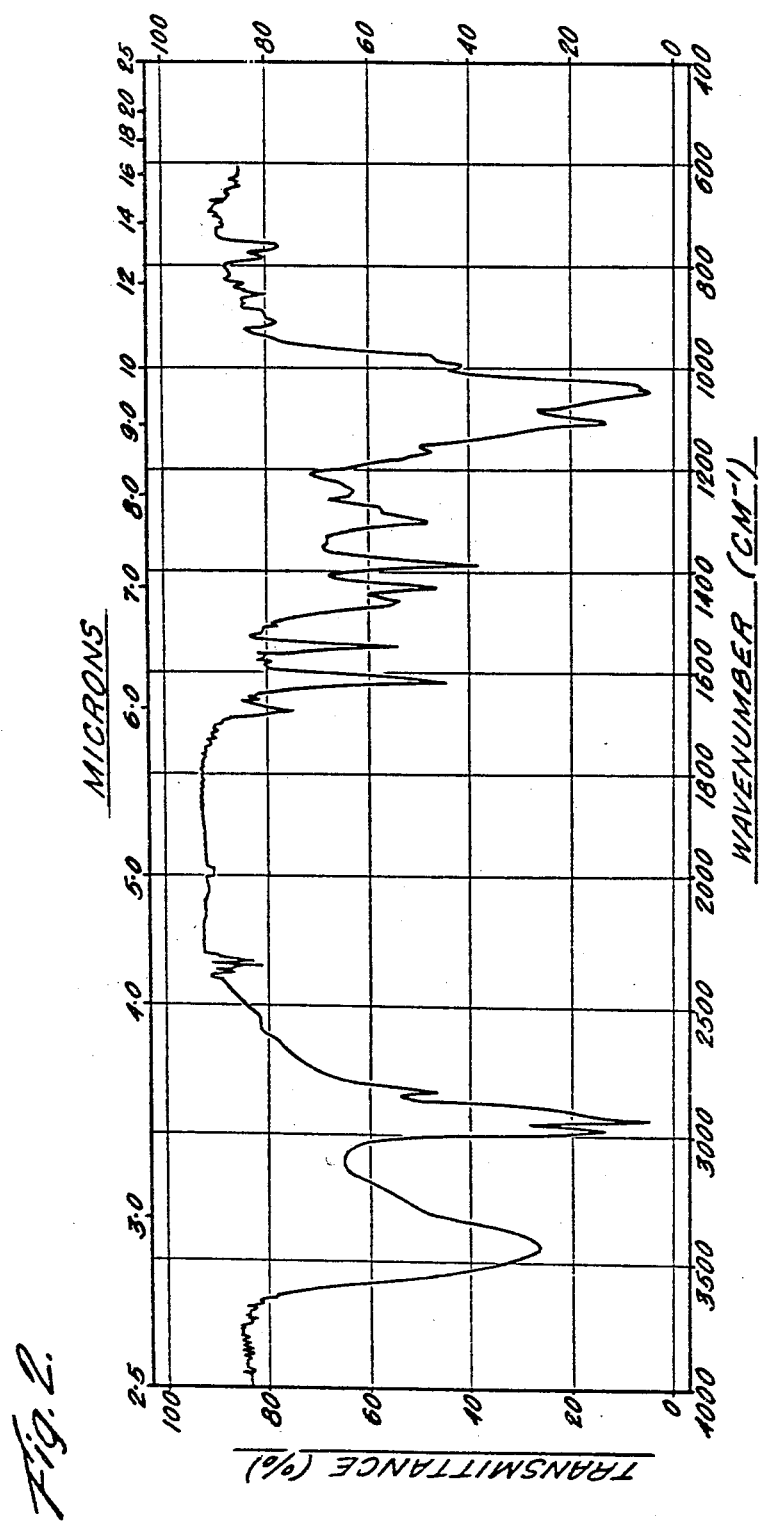
Figure 3:
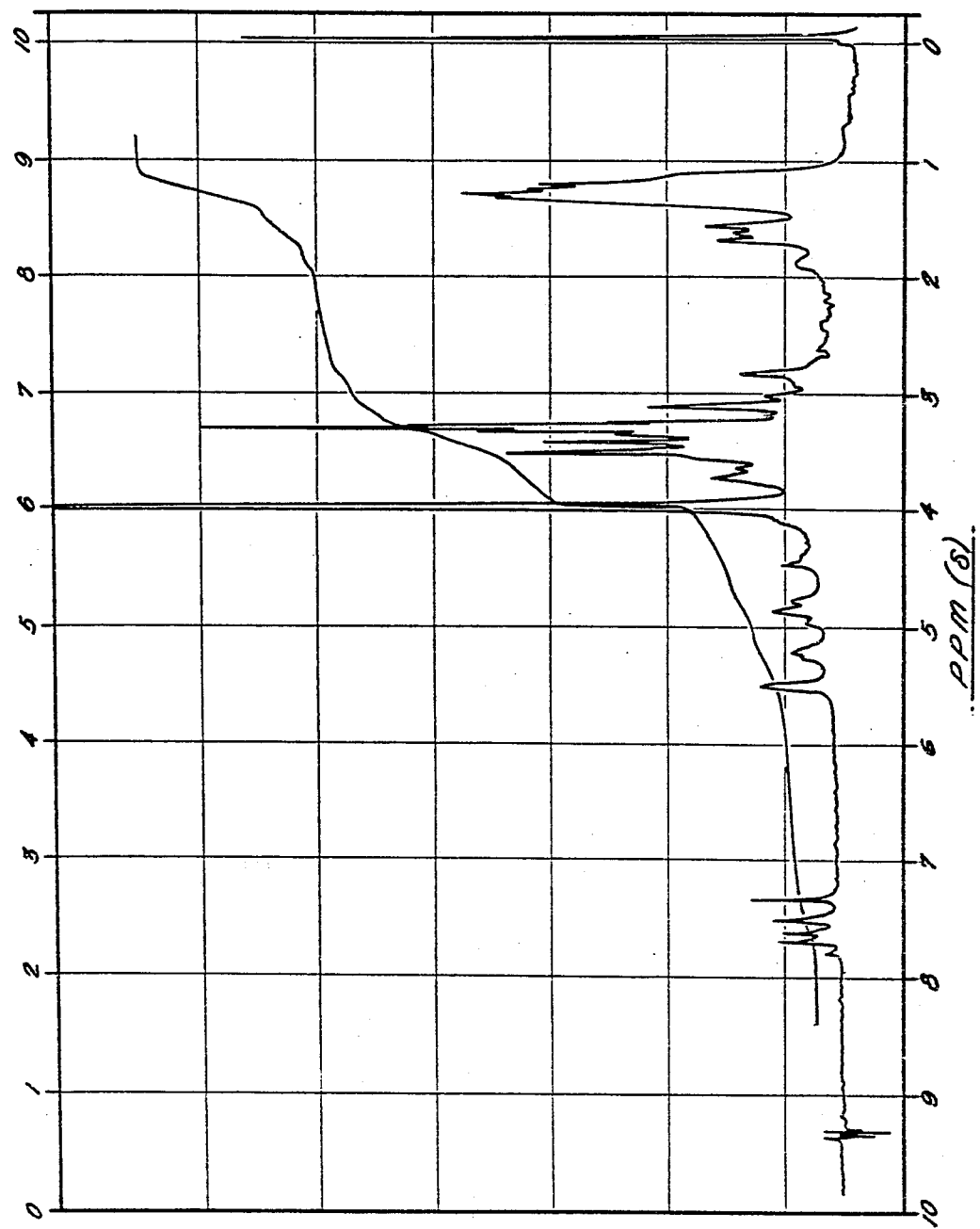

FRAGILOMYCIN A (a) red-orange solid having a melting point of 197°–199° C. (dec.);

(b) approximate elemental composition of 55.07 percent carbon, 6.92 percent hydrogen and 2.37 percent nitrogen;

(c) proposed empirical formula of $C_{54}H_{82}N_2O_{26}$;

(d) specific optical rotation: $[\alpha]_D = +29.5°$ (C=0.1 methanol);

(e) solubility: soluble in methanol, methylene chloride and dimethyl sulfoxide; sparingly soluble in water at a pH of 6.0 or lower;

(f) ultraviolet absorption spectrum in methanol exhibits absorption maxima at 438 nm, 296 (sh) nm, 264 nm, 231 nm, and 208 nm, as shown in FIG. 1;

(g) infrared absorption spectrum in KBr exhibits peaks at the following wavelengths in $cm^{-1}$: 3430, 2970, 2930, 2820, 1671, 1613, 1547, 1455, 1430, 1385, 1300, 1105 and 1045 as shown in FIG. 2;

(h) proton magnetic resonance spectrum in $CDCl_3$—$CD_3OD$ (80 MHz) shows the following chemical shifts (ppm) 7.4–8.2 (multiplet), 4.0 (singlet), 3.8 (doublet), 3.5 (multiplet), 3.2 (singlet) and 1.2 (doublet) as shown in FIG. 3;

(i) field desorption mass spectrum at 20 ma exhibits the following fragmentation pattern (m/e) 892, 872-871, 824 and 392.

DEGRADATIVE STUDY

The structure of fragilomycin A was confirmed through a degradative study as follows:

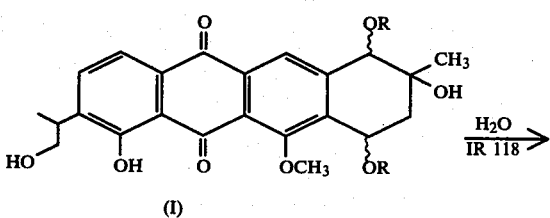

(I)

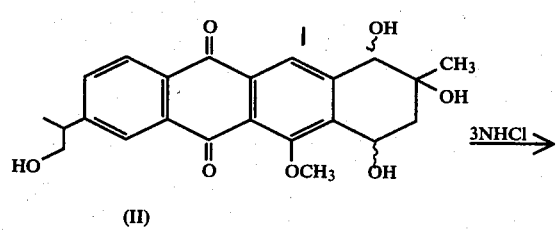

(II)

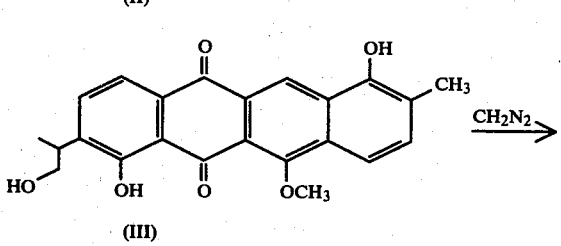

(III)

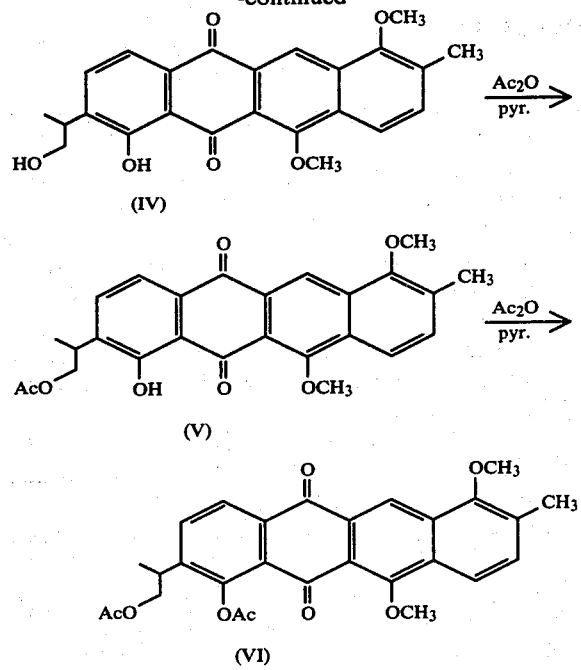

The aglycone of fragilomycin A, Structure (II), was obtained by hydrolyzing fragilomycin A (I) in water and an acidic cation exchange resin. Fragilomycin A bis-anhydroaglycone (III) may be prepared from either fragilomycin A or fragilomycin A aglycone by hydrolysis in 3 N hydrochloric acid. Monomethyl fragilomycin A bisanhydroaglycone (IV) was prepared from compound (III) with diazomethane. The reaction of compound (IV) with acetic anhydride (Ac₂O) in the presence of pyridine affords both monomethyl fragilomycin A bisanhydroaglycone monoacetate (V) and monomethyl fragilomycin A bisanhydroaglycone diacetate (VI) in a stepwise manner. The structures of the compounds of the Structures (III) to (VI) were confirmed by a combination of infrared absorption spectroscopy, ultraviolet absorption spectroscopy, mass spectroscopy, and proton magnetic resonance spectroscopy.

The preparation of the novel anthracycline antibiotics of the present invention is described below.

THE MICROORGANISM

*Streptosporangium fragile* Shearer sp. nov. SK&F BC2496 (ATCC 31519) is a Gram-positive, not acid fast organism that forms a distinct mycel m. Analyses of whole cell hydrolysates by the method of Becker [Becker et al., Appl. Microbiol. 12, 421–23 (1964)] indicate that the cell walls contain the meso-isomer of 2,6-diaminopimelic acid and have a sugar pattern of type B with madurose present as the characteristic sugar [Lechevalier et al., Int. J. Syst. Bacteriol. 20, 435–43 (1970)]. The microorganism has a phospholipid composition of type PIV [Lechevalier et al., Biochem. System. Ecol. 5, 249–60 (1977)].

Round sporangia, usually 6–12 μm in diameter are formed on the aerial mycelium. These may be born apically on the main thread or on very short to relatively long lateral branches; a few appear to be sessile. The sporangiospores are arranged in a coil within the sporangium. The spores are spherical to ovoid and non-motile. The sporangial membranes are unusually fragile and in older cultures this results in the coalescence of the spores into large irregular masses. No violet crystals of iodinin are formed. No vitamins are required by *S. fragile* for growth.

The description of *S. fragile* on various media follows. All cultures were incubated at 28° C. and observed for 21 days. The colors for the culture were chosen by comparison with chips from either the ISCC-NBS Centroid Color Charts or the Munsell Book of Color.

Yeast Extract-Malt Extract Agar—growth excellent; reverse black; aerial mycelium-scant to moderate, white turning pink; sporangia abundant; brown soluble pigment.

Oatmeal Agar—growth good; vegetative growth black (ISCC-NBS 267, black); reverse black; aerial mycelium-moderate, white turning light pink (ISCC-NBS 8, grey pink); sporangia abundant; light brown soluble pigment.

Inorganic Salts-Starch Agar—growth good; vegetative growth brown black (ISCC-NBS 65, brown black); reverse black; aerial mycelium-moderate, white turning light pink (Munsell 5R 9/2); sporangia abundant; light brown soluble pigment.

Thin Potato Carrot Agar—growth fair, flat; reverse black; aerial mycelium-sparse, white turning light pink; sporangia abundant; light brown soluble pigment.

Glycerol Asparagine Agar—growth fair, flat; reverse brown; aerial mycelium-sparse; sporangia-none to sparse; light brown soluble pigment.

Tyrosine Agar—growth fair; reverse brown; aerial mycelium-sparse, white; no sporangia; light brown soluble pigment.

Potato Dextrose Agar—growth fair to good; reverse black; aerial mycelium-abundant, white turning pink (Munsell 2.5 YR 9/2); sporangia abundant; light brown soluble pigment.

Czapek-Sucrose Agar—growth poor, flat; reverse brown; aerial mycelium-scant; no sporangia; light brown soluble pigment.

Bennett's Agar—growth good; reverse black; no aerial mycelium; brown soluble pigment.

Czapek-Peptone Agar—growth fair; reverse brown; no aerial mycelium; light brown soluble pigment.

Emerson's YpSs Agar—growth good; reverse black; aerial mycelium-scant, white; no sporangia; brown soluble pigment.

M172 Agar—growth excellent; reverse black; aerial mycelium-none to scant; sporangia few to moderate; brown soluble pigment.

Defined Agar—no growth.

The brown soluble pigment is known to be a mixture of a number of pigments which together give the impression of brown.

Stock cultures of *S. fragilis* were grown on Medium 172 at 28° C. The physiological tests employed in characterizing the culture were those of Gordon [Gordon, J. Gen. Microbiol. 45 355-64 (1966)] and Gordon and Mihm [Gordon et al., Ann. N.Y. Acad. Sci. 98, 628-36 (1962)]. All plate media were observed for 21 days and tubed media were observed for 28 days.

The biochemical and physiological characteristics of the *S. fragile* are as follows.

No growth takes place under anaerobic conditions. Temperature range for growth is 15° C. to 45° C. No growth occurs at 10° C. or 50° C. Hydrogen sulfide is produced. Milk is peptonized. Gelatin is hydrolyzed, but not liquified. Nitrate is reduced to nitrite. Starch, casein, L-tyrosine and hypoxanthine are hydrolyzed but urea, adenine and xanthine are not. Catalase is produced, Esculin is decomposed. Acid is produced from dextrose, D-arabinose, L-arabinose, D-cellobiose, D-fructose, D-galactose, lactose, D-mannitol, D-mannose, D-ribose, rhamnose, salicin, soluble starch, trehalose, D-xylose, i-erthyritol, α-methyl-D-glucoside, dextrin, glycogen and maltose. No acid is produced from dulcitol, glycerol, i-inositol, melibiose, D-melezitose, raffinose, D-sorbitol, L-sorbose, sucrose, adonitol, inulin, or α-methyl-D-mannoside. Citrate, malate, succinate, lactate, and pyruvate are utilized. Benzoate, formate, tartrate and oxalate are not utilized. Utilization of propionate and acetate is variable.

The above-described microorganism was concluded not to agree with the description of any known species of Streptosporangium. Hence, it is described as new under the name *Streptosporangium fragile* Shearer sp. nov. The specific epithet refers to the fragility of the sporangial wall.

PREPARATION OF THE FRAGILOMYCIN COMPLEX

Fragilomycin complex may be produced by cultivating a strain of Streptosporangium having the characteristics of ATCC 31519 or a mutant thereof under submerged aerobic conditions in an aqueous nutrient medium. The organism is grown in a nutrient medium containing an assimilable carbon source, for example an assimilable carbohydrate. Examples of suitable carbon sources include sucrose, lactose, maltose, mannose, fructose, glucose, and soluble starch. The nutrient medium should also contain an assimilable nitrogen source such as fish meal, peptone, soybean flour, peanut meal, cotton seed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of the fragilomycin complex can be effected at any temperature conducive to satisfactory growth of the organism, e.g., 15°–45° C., and is conveniently carried out at a temperature of about 28° C.

The medium normally is neutral, but the exact pH can be varied between 5.0 and 7.5 depending on the particular medium used.

The fermentation may be carried out in Erlenmeyer flasks or in laboratory or industrial fermentors of various capacities. When tank fermentation is to be used, it is desirable to produce a vegetative inoculum in a nutrient broth by inoculating a small volume of the culture medium with the vegetative cells of the organism. After obtaining an inoculum in this manner, it is transferred aseptically to the fermentation tank medium for large scale production of the antibiotics. The medium used for the vegetative inoculum can be the same as that employed for larger fermentations, although other media can be employed.

As is customary in aerobic submerged culture processes, sterile air is sparged through the culture medium. Agitation may be maintained by means of agitard generally familar to those in the fermentation industry.

In general, optimum production of the complex is achieved after incubation periods of about 72–168 hours in stir-jar fermentors or tank fermentors. The course of the fermentation can be followed by assaying the fermentation medium from time to time against an organism susceptible to the fragilomycin complex, e.g., *Staphylococus aureus* 209P or *Salmonella gallinarum* ATCC 9184.

The fragilomycin complex may be recovered from the fermentation medium by extraction with a water-immiscible organic solvent, preferably a polar organic solvent such as ethyl acetate, methyl isobutyl ketone, and most preferably methylene chloride.

The majority of the antibiotic activity is found in the vegetative mycelium of the culture. Diatomaceous earth is added to the fermentation medium and the entire batch filtered. The filter cake containing the vegetative mycelium is then extracted with a polar organic solvent, such as, acetone or methanol. The extract is evaporated in vacuo to afford the desired crude fragilomycin complex.

SEPARATION AND ISOLATION OF FRAGILOMYCIN COMPLEX

The anthracycline antibiotic, fragilomycin complex can be separated from the other components of the crude fragilomycin complex by chromatography of solutions on columns packed with a suitable adsorbent such as Sephadex LH20 (trade name for dextran derivatives used as gel filtrants in organic solvents, manufactured by Pharmacia Fine Chemicals, Inc.). The components are then eluted from the adsorbent with a suitable organic solvent such as methanol. Multiple fractions are collected and inhibitory activity against the growth of *Bacillus subtilis* is measured by an agar-disc assay. The appropriate fractions, as determined by disc diffusion assay are combined and evaporated to dryness to afford the fragilomycin complex. The fragilomycin complex may be further purified by chromatography of solutions on columns packed with a silica gel adsorbent, such as Silica Gel 60, particle size 0.040–0.063 mm (trade name for adsorbent manufactured by E. Merck, Darmstadt). The antibiotic is then eluted from the adsorbent with suitable solvents such as mixtures of 4 to 20% methanol in methylene chloride. Multiple fractions are collected and inhibitory activity against the growth of *B. subtilis* is measured by an agar-disc assay. The appropriate fractions, as determined by disc diffusion assay, are combined and evaporated to give essentially pure fragilomycin A. This material was further purified by an additional chromatography from a column packed with Whatman Partisil 10 PAC and by reprecipitation from methylene chloride-diethyl ether to yield pure fragilomycin A.

Biological Activity Data

The in vitro minimum inhibitory concentration (MIC) of crude fragilomycin complex, fragilomycin complex and fragilomycin A was determined for a number of microorganisms using the standard tube dilution procedure.

Antimicrobial Spectrum

| | MIC in μg/ml | | |
|---|---|---|---|
| Test Organism | Crude Fragilomycin Complex | Fragilomycin Complex | Fragilomycin A |
| *Staphylococcus aureus* HH 127 | 31 | ~2.0 | 8 |
| *Staphylococcus aureus* SA 910 | 16 | 4 | 4 |

-continued

| Test Organism | MIC in μg/ml | | |
|---|---|---|---|
| | Crude Fragilomycin Complex | Fragilomycin Complex | Fragilomycin A |
| Streptococcus faecalis HH 34358 | 4 | 0.5 | 2 |
| Escherichia Coli SKF 12140 | NT | >250 | 63 |
| Klebsiella pneumoniae SKF 4200 | NT | >250 | 8 |
| Bacteroides fragilis fragilis ATCC 25285 | 63 | NT | 6.2 |
| Bacteroides fragilis fragilis H-76 | 250 | NT | >25 |
| Bacteroides fragilis fragilis H-152 | 63 | NT | 6.2 |
| Bacteroides fragilis fragilis H-154 | 63 | NT | 6.2 |
| Bacteroides fragilis vulgatus H-53 | 31 | NT | 6.2 |
| Bacteroides fragilis ovatus H-11 | >500 | NT | >25 |
| Bacteroides fragilis distasonis H-111 | >500 | NT | >25 |
| Bacteroides fragilis thetaiotamicron H-55 | 31 | NT | 6.2 |
| Bacteroides fragilis thetaiotamicron H-73 | 63 | NT | 6.2 |
| Bacteroides fragilis thetaiotamicron H-89 | NT | NT | >25 |
| Bacteroides fragilis thetaiotamicron H-145 | 31 | NT | >25 |
| Fusobacterium A.T.C.C. 25586 | NT | NT | >25 |
| Clostridium perfringes A.T.C.C. 19408 | 63 | NT | 0.8 |
| Clostridium perfringes MCP-1 | 63 | NT | 0.8 |
| Clostridium perfringes MCP-2 | 63 | NT | 0.8 |

NT = Not tested

The crude fragilomycin complex exhibits in vivo activity against S. aureus HH 127 and is useful in controlling bacterial infections in animals and humans. Male albino Swiss mice, weighing 18 to 20 grams, were infected intraperitoneally with 2.3 $LD_{50}$ of S. aureus HH 127 diluted in hog gastrin mucin to produce uniformly lethal infection. The crude fragilomycin complex was administered subcutaneously at 1 hour and 5 hours after infection. The final survival percentages for the group of 10 mice were obtained after 3 days observation. These percentages were used to calculate the $ED_{50}$ of the crude fragilomycin complex. The $ED_{50}$ of the crude fragilomycin complex, determined by the method of Litchfield and Wilcoxon [J. Pharmacol. Exp. Ther. 96 pp. 99–113 (1949)] was 30 mg/kg.

The antibiotic compounds of the present invention including fragilomycin complex and its major bioactive component, fragilomycin A, and mixtures thereof, exhibit antibacterial activity. The invention includes within its scope pharmaceutical compositions containing at least one of the above-mentioned antibiotic compounds and pharmaceutically acceptable carrier. The compositions may also contain other active antibacterial agents. The compositions may be made up in any pharmaceutical form appropriate for the route of administration in question. Such compositions are exemplified by solid compositions for oral administration, such as tablets, capsules, pills, powders and granules; liquid compositions for oral administration such as solutions, suspensions, syrups and elixers; and preparations for parenteral administration such as sterile solutions, suspensions or emulsions.

For use as an antibacterial agent, the compositions are administered so that the concentration of the active ingredient is greater than the minimum inhibitory concentration for the particular organism being treated.

The following examples are illustrative of the prsent invention and are not therefore to be considered in limiting the present invention as described in the claims appended hereto.

The nutrient media employed in the following examples have the compositions listed below.

M 172 Agar slant medium—glucose, 10 g; soluble starch, 20 g; yeast extract, 5 g; N-Z amine type A, 5 g; $CaCO_3$, 1 g; agar, 15 g, and distilled water 1 L.

Medium 13—soluble starch, 30 g; sucrose, 10 g; dextrose, 10 g; soy peptone, 15 g; corn steep liquor, 10 g; $K_2HPO_4$, 3 g; NaCl, 1 g; $CaCO_3$, 3 g; distilled water, 1 L and mineral solution, 10 ml—$ZnSO_4.7H_2O$, 2.8 g; $Fe(NH_4)_2HC_6H_5O_7$, 2.7 g; $CuSO_4.5H_2O$, 0.125 g; $MnSO_4.H_2O$, 1 g; $CoCl_2.6H_2O$, 0.1 g; $NaB_4O_7.H_2O$, 0.09 g; $Na_2MoO_4.2H_2O$, 0.05 g; distilled water, 1 L.

Medium L-7-glucose, 45 g; pharmamedia (Industrial grade of cotton seed flour by Traders Oil Mill Company, Fort Worth, Texas), 20 g; $(NH_4)_2SO_4$, 3 g; NaCl, 2 g; $CaCO_3$, 3 g; amber BYF, 2 g; and tap water, 1 L.

Stock cultures of S. fragile were grown on M 172 agar slant medium at 28° C.

EXAMPLE 1

After from 2 to 4 weeks growth at 28° C., cells from the stock culture were transferred to a 50 ml test tube containing 10 ml of medium 13. The cells were incubated at 28° C. on a reciprocal shaker for 3 days to form a seed culture. A one ml. aliquot of the seed culture was then transferred to a shaker tube containing 10 ml of medium 13. After 3 days incubation at 28° C. on a reciprocal shaker, the anthracycline complex was detected in the clarified broth, cell extracts and whole broth concentrates by using either Staphylococcus aureus 209P or Salmonella gallinarum ATCC 9184 in a disc diffusion assay.

EXAMPLE 2

After from 2 to 4 weeks growth at 28° C., cells from the stock culture were employed to innoculate a 500 ml Erlenmeyer flask containing 100 ml of medium 13.

After incubation on a rotatory shaker, 250 rpm, at 28° C. for 3 days, 30 ml of the mature culture was then employed to innoculate a 2 l. Erlenmeyer flask containing 300 ml of either medium 13 or medium 7. After 3 days incubation at 28° C. on the rotatory shaker, the anthracycline complex was detected in the whole broth, clarified broth and broth concentrate via disc diffusion assay employing a number of gram-positive assay organisms.

EXAMPLE 3

A 14 l. glass vessel fermentor (New Brunswick Model 19) with 10 l. of sterile production medium L-7 was aseptically inoculated with 1000 ml of vegetative culture (prepared as in Example 2 except a 4 l. aspirator bottle containing 1000 ml of medium 13 was used). The vessel was operated according to the following schedule:

| Agitation: | 500 rpm | from 0–138 hr. |
|---|---|---|
| Aeration: | 0.5 V/V/M | from 0–138 hr. |
| Temp.: | 28° C. | |

*V/V/M — vol. of air per vol. of medium per minute.

The tank was harvested at the peak activity using *Staphylococcus aureus* 209P and *E. coli* ss (SK&F AAA-308) as test strain s.

EXAMPLE 4

The 70 l. tank fermentation (Fermentation Design) was run in similar fashion to Example 3. The three day culture broth in the 14 l. vessel with medium 13 was used to inoculate the 70 l. fermentor containing 45 l. of L-7 medium. The fermentation apparatus was operated as follows:

| Agitation: | 250 rpm from | 0–91 hr. |
|---|---|---|
| | 350 rpm from | 91–98 hr. |
| | 400 rpm from | 98–139 hr. |
| Aeration: | 0.5 v/v/m from | 0–91 hr. |
| | 0.7 v/v/m from | 91–139 hr. |
| Temp.: | 28° C. | |

EXAMPLE 5

The 450 l. fermentor (Chemapec) was operated in similar fashion to Example 4. Inoculum from the 14 l. vessel with medium 13 was transferred to 70 l. fermentor (Chemapec) filled with 50 l. of medium 13. The fermentation was conducted as follows:

| Agitation: | 350 rpm from | 0–18 hr. |
|---|---|---|
| | 400 rpm from | 18–73 hr. |
| Aeration: | 0.4 v/v/m from | 0–18 hr. |
| | 0.5 v/v/m from | 18–73 hr. |
| Temp.: | 28° C. | |

The 450 l. fermentor contained 300 l. L-7 medium, was inoculated with the three-day culture broth from a 75 l. vessel and was operated as follows:

| Agitation: | 300 rpm from | 0–24 hr. |
|---|---|---|
| | 400 rpm from | 24–136 hr. |
| Aeration: | 0.4 v/v/m from | 0–89 hr. |
| | 0.5 v/v/m from | 89–136 hr. |
| Temp.: | 28° C. | |

EXAMPLE 6

Screen for Initial Isolation Fragilomycin Complex

Five hundred mls of broth from a shake flask culture in medium 13 were treated as follows: two 10 ml aliquots of the broth were removed, one as a representative sample of the whole broth, and the other, after centrifugation at 500×g, 4° C. for 20 minutes and decantation as an example of centrifuged broth. The remainder of the broth was treated with Hyflo Super Cel at a ratio of 1 g to 100 mls, stirred and filtered through a Buchner funnel. The clear filtrate was defined as clarified broth. Samples of all three treatments were disced against agar plates, seeded with sensitive gram-positive and gram-negative organisms.

Concomitantly, 5 ml aliquots of the clarified broth were extracted over a range of pH with ethyl acetate (2×5 ml). After removal from the aqueous layer, the extracts at each pH were combined, dried over sodium sulfate and evaporated under reduced pressure, finally being made to 0.5 ml (a formal 10 fold concentration) with ethyl acetate and disced against a range of organisms. Following adjustment of their pH to neutrality, the extracted aqueous solutions were also disced as above.

In addition, further 5 ml aliquots of clarified broth were chromatographed on small (7 mm×30 mm) columns of various adsorbents, including, but not limited to, Charcoal, Macroreticular Resins (XAD's; Rohm and Haas, Phila., Pa.) and Ion Exchangers. The effluents and eluants were also disced as above.

All seeded assay plates were incubated at 28° C. for 16 hrs., and following evaluation of the data, an XAD-2 resin was judged the best isolation method for larger scale use.

EXAMPLE 7

Larger Scale Isolation and Paper Chromatography of Fragilomycin Complex

Two hundred and twenty mls of clarified broth from a 500 ml shake flask culture (vide Example #6) were passed through a 40 ml column of XAD-2 resin (Rohm and Haas, Phila. Pa.) in water. The effluent broth, approximately 200 mls, was kept and the column was further washed with 1 liter of water, which was discarded. The antibacterial activity was eluted by development with 250 mls of absolute methanol. This fraction was evaporated under reduced pressure at less than 40° C., to give 600 mg of a crude brown oil, which was redissolved in 3 mls of 50:50 v/v methanol:water and disced together with the effluent, against a suitable range of microorganisms. Inspection of the seeded plates after overnight incubation at 37° C. indicated that the extract had antibacterial activity against *B. subtilis*, *S. aureus* and *Salmonella gallinarum*.

The nature of the extract was further investigated by means of paper chromatography followed by bioautography against *B. subtilis*. Thus, 20 μl aliqouts of the extract were spotted on Whatman #1 paper and developed at 20° C. in the manner indicated in the following table. Chloramphenicol (Sigma Chemical Co., St. Louis, Mo.) was used as an external standard in all chromatography. Following development, the sheets were air-dried at 20° C., placed on seeded agar trays containing 0.01% triphenyl tetrazolium chloride. After 30 minutes, the sheets were removed, the agar surfaces were covered and the bioautography trays were incubated at 37° C. for 16 hrs.

| Solvent | Water | n-Butanol Satd. w H₂O | Ammonium Chloride 3% w/v | n-Butanol: Methanol: H₂O 4:1:2 v/v/v | Benzene: Methanol 4:1 v/v |
|---|---|---|---|---|---|
| Type | Downward | Downward | Downward | Downward | Upward |
| Time | 3.5 hrs. | 10 hrs. | 3.5 hrs. | 10 hrs. | 3 hrs. |
| $R_f$ Chloramphenicol | 0.78 | 0.77 | 0.80 | 0.84 | 0.52 |
| $R_f$ Extract | Streak; 0.0–0.62 | Streak; 0.06–0.81 | 0.50 | 0.81 | 0.91 |

EXAMPLE 8

Recovery of Fragilomycin

To 8.2 liters of culture obtained according to Example 3, diatomaceous earth was added and the batch filtered; 5.2 liters of clarified broth was obtained, and the filter cake containing the vegetative mycelium of the culture was retained. The filter cake was extracted with 2 liters of acetone, and the extract evaporated in vacuo at 35° C. to yield 18.92 g product. The broth was determined to contain 126.51 g product, as dry weight. Microbiological assay against *Bacillus subtilis* demonstrated that the 5.2 liters of clarified broth (126.51 g) contained 20,242 units of activity and the 18.92 g of acetone extraction product of the vegetative mycelium 99,578 units of activity. Chromatography of these products on Whatman #1 paper, developed in a mixture of benzene:methanol (4:1), ascending, for 4½ hrs, and bioautography against *Bacillus subtilis* demonstrated the presence of the desired product, in both broth and vegetative mycelial extract, at $R_fO$ on the bioautogram.

EXAMPLE 9

Large Scale Recovery of Crude Fragilomycin Complex

Three hundred and forty liters of culture obtained according to Example 6 was filtered through a layer of diatomaceous earth on a rotary vacuum filter; the clarified broth was discarded and the filter cake containing the vegetative mycelium of the culture was lyophilized. The lyophilized vegetative mycelium, total weight obtained was 14 kg, was extracted with 84 liters of methylene chloride. The extract was evaporated, in vacuo at 35° C., and yielded 54.5 g of inactive material which was discarded. The lyophilized vegetative mycelium was then extracted with 84 liters of methanol. The methanol extract, on evaporation in vacuo at 35° C., yielded 638 g of crude antibiotic complex.

EXAMPLE 10

Large Scale Separation of Fragilomycin Complex

Two hundred grams of the crude antibiotic complex from Example 9 was stirred with 1.6 liters of methanol at room temperature for 45 min. and filtered; 51.3 g of insoluble, inactive material was discarded. The methanolic solution, containing 149.7 g product, was mixed with 264 g silica gel (E. Merck; 40–63μ) and the mixture was dried in vacuo at 35° C. The dried mixture was chromatographed by addition to the top of a silica gel column 8 cm in diameter containing 1.5 Kg silica gel (E. Merck, 10–40μ); operating conditions: 8 bars column packing pressure, 8–9 bars solvent delivery pressure, flow rate 100–200 ml/min. The column was eluted with 5 liters each of the following solvents in this sequence: methylene chloride, methanol:methylene chloride (0.5:9.5), (1:9), (2:8), (3:7), (1:1), (7.5:2.5), and methanol. Eluant fractions were collected, approximately 0.5 liter volumes, and antibiotic activity determined by assay against appropriate microorganism. The methanol:methylene chloride (1:9) fractions (51–71) were combined, evaporated in vacuo at 35° C., to yield 7.94 g of the crude fragilomycin complex [$R_fO$ /Whatman #1, ascending, benzene:methanol (4:1)].

EXAMPLE 11

Fractionation of Fragilomycin Complex

One hundred g of Sephadex LH-20, soaked in methanol for a minimum of 24 hrs was slurry packed in a column, 25×780 mm. The product (325 mg) obtained from Example 10 was dissolved in methanol and applied to the column which was then developed with methanol by downward flow. The eluate was collected at approximately 2.5 ml/min in 15 ml fractions. The fractions were sampled by conventional discing techniques and activity against *B. subtilis* was measured. Those fractions of similar zone size were combined, evaporated and assayed by disc dilution assay (against Staph. 209P) as follows:

| Fraction No. | Wt. on Evaporation | DDC* (mg/ml) |
|---|---|---|
| 1–5 | — | 10 |
| 6–13 | 48 mg. | 4.8 |
| 14–24 | 71 mg | 0.055 |
| 25–28 | 12 mg | 0.19 |
| 29 (~250-ml fractions) | 73 mg | 0.90 |
| 30 (~250-ml fractions) | 42 mg | >10 |
| 31 (~250-ml fractions) | 63 mg | >10 |

*disc dilution concentration

The most active fraction was further chromatographed on silica gel as follows: An Altex medium pressure glass column, 15×250 mm, was filled with Silica Gel 60 (E. Merck, 230–400 mesh) fragilomycin complex, 82 mg obtained from chromatography on Sephadex LH20, was dissolved in 4% methanol in methylene chloride and applied to the column which was developed by upward flow at a flow rate of approximately 2–3 ml/min. A step-wise gradient of elution was used as follows:

| % Methanol in methylene chloride | Volume (ml) |
|---|---|
| 4 | 100 |
| 6 | 50 |
| 8 | 200 |
| 10 | 3000 |
| 20 | 1000 |

Fractions of 20 ml volume were collected and disced for antibiotic activity against *B. subtilis*. Those fractions of similar zone size were combined, evaporated and assayed by disc dilution assay against Staph. 209P as follows:

| Fraction | Tube No. | Wt. on Evaporation (mg) | DDC (mg/ml) |
|---|---|---|---|
| A | 1–50 | 17 | 1.06 |
| B | 51–60 | 6 | 0.75 |
| C | 66–120 | 69 | 0.05 |
| D | 121–130 | 9 | 1.10 |
| E | 130–180 | 28 | 3.50 |
| F | 181 (1000 ml) | 14 | 3.50 |

The most active fraction (c) was dissolved in a solution of 6% methanol in methylene chloride and chromatographed on a column (9.4×500 mm) containing Whatman Partisil 10 PAC using an eluting solvent of 6% methanol in methylene chloride. The major component, as determined by ultraviolet absorption at 254 nm, was collected and reprecipitated twice from methylene chloride-diethyl ether to afford pure fragilomycin A.

What is claimed is:

1. A biologically pure culture of the microorganism *Streptosporangium fragile* Shearer sp. nov. ATCC 31519, said culture being capable of producing fragilomycin A in recoverable quantity upon cultivation in an aqueous nutrient medium containing assimilable sources of nitrogen and carbon.

2. A culture of the microorganism according to claim 1, which is capable of producing an antibiotic complex containing fragilomycin A.